United States Patent [19]
De March et al.

[11] Patent Number: 5,279,959
[45] Date of Patent: Jan. 18, 1994

[54] PROCESS FOR THE PRODUCTION OF SUBSTANCES OF VEGETABLE ORIGIN

[75] Inventors: Ghislaine De March, St-Cyr sur Loire; Jean Hariel, Vetraz-Monthoux; Vincent Petiard, Tours, all of France

[73] Assignee: Nestec S.A., Vevey, Switzerland

[21] Appl. No.: 405,337

[22] Filed: Sep. 11, 1989

[30] Foreign Application Priority Data

Sep. 19, 1988 [EP] European Pat. Off. ........ 88115354.8

[51] Int. Cl.$^5$ .............................................. C12N 5/04
[52] U.S. Cl. ............................ 435/240.45; 435/240.51
[58] Field of Search ............. 435/240.4, 240.45, 240.51

[56] References Cited

U.S. PATENT DOCUMENTS 4,910,138  3/1990  Miura et al. ...................... 435/119

FOREIGN PATENT DOCUMENTS 3138493  9/1981  Fed. Rep. of Germany.

OTHER PUBLICATIONS

Augereau et al., (1986), Plant Cell Rep., 5:372-376.
Banthorpe et al., (1988), Phytochemistry, 27:795-801.
Hashimoto et al., (1987), Agric. Biol. Chem., 51(10):2769-2779.
Miller et al., (1987), Gamete Research, 17:57-61.
Bisson et al., *Production of Essential Oils by Cells Suspensions of Chamomile in a Two-Phase System*; (1983), Planta Medica, 47:164-168.
French Translation of Japanese Patent No. 5739778, (1982); Inventors: Yasuhiro, et al.
Takeda et al., "Growth and Sesquiterpenoid Production by *Calypogeia granulata* Inoue Cells in Suspension Culture", Planta, (1981), 151:525-530.
Nagel et al., "The Volatile Oil of the Callus Cultures of *Ruta graveolens*, II. Physiology of Production of the Volatile Oil", Planta Medica, vol. 27, (1975), pp. 264-270.
Nagel et al., "The Volatile Oil of Callus Cultures of *Ruta graveolens* L., I. The Composition of the Oil", Planta Medica, vol. 27, 1975, pp. 151-158.

*Primary Examiner*—Che S. Chereskin
*Attorney, Agent, or Firm*—Vogt & O'Donnell

[57] ABSTRACT

To produce substances of vegetable origin, a vegetable organ is implanted in a culture medium and is kept under hypoxia by immersion beneath a layer of oil and the substances produced are extracted from the organ, the medium and/or the oil.

12 Claims, No Drawings

PROCESS FOR THE PRODUCTION OF SUBSTANCES OF VEGETABLE ORIGIN

BACKGROUND OF THE INVENTION

This invention relates to a process for the production of substances of vegetable origin by "in vitro" culture.

Numerous substances of vegetable origin have a certain economic value for such industries as the pharmaceutical industry (active principles of medicaments), the cosmetics industry (perfume) and the food industry (flavourings and additives). The substances in question are generally produced by extraction from collected or cultivated plants. However, this method has many disadvantages, particularly in regard to restocking of the vegetable starting material (periodicity, stability, quality, etc.).

Various substitute processes have been investigated with a view to obviating these disadvantages. They include the "in vitro" process for culturing undifferentiated tissues or cells of productive species. Reference is made in this regard to Japanese patent JP 57-39778, which relates to the culture of calluses in an agitated liquid medium containing cellulose to extract the active principles therefrom with paraffin oil and/or fats, and to the Article by Bisson et al (Journal of Medicinal Plant Research, 1983, 47, 164) which relates to the extraction of essential oils from a culture of undifferentiated cells of camomile by addition to the nutrient medium of droplets of a fatty phase in which the oils are to accumulate. However, because they use undifferentiated cells, these techniques are limited to the preparation of well-defined products.

SUMMARY OF THE INVENTION

The object of the present invention is to combine the advantages of the differentiated system with those of "in vitro" culture.

To this end, the process according to the invention is characterized in that
- a vegetable organ is implanted in a culture medium and
- is kept under anoxia or hypoxia by immersion beneath a layer of oil.

The substances produced are preferably extracted from the vegetable organ, from the culture medium and/or from the oil. Conventional extraction techniques may be used for this purpose. The main advantage of the process lies in the "in vitro" culture of vegetable organs producing the desired substances and in their sustenance and their production of these substances over long periods.

The oil used to maintain hypoxia may enable possible losses of volatile substances to be avoided and the substances in question to be extracted.

One advantage of this invention is that it enables the substances to be produced in a constant and reproducible manner.

Another advantage of the invention is that it enables the production phase of the substances by vegetable organs to be sustained for much longer periods than the normal duration of "in situ" production by plants.

Another advantage of the invention is that it enables the vegetable organ to retain its specific qualitative characteristics, which is rarely the case with undifferentiated cell cultures where secondary substances may be produced.

In this way, the vegetable organs not only do not become cankered and survive for several months, they also continue to accumulate in their tissues, the culture medium and the hypoxia oil such substances as essential oils identical or similar in nature to those produced by traditional methods of extraction from plants

DETAILED DESCRIPTION OF THE INVENTION

The process according to the invention is concerned with the sustenance of vegetable organs and not with the growth and/or proliferation of tissues, although this may occur to a reduced extent in certain cases.

Suitable criteria for evaluating the survival of the vegetable organ include
- as appearance criteria:
  - the development of pigmentation in the implant
  - the appearance of chlorosis or browning (oxidation),
- as morphological criteria:
  - blooming
  - the appearance of calluses and/or roots.

These criteria are evaluated in different ways, namely:
- visually
- by biochemical tests (coloration test, etc.), which enable the viability of the organ to be assessed.

The vegetable organs cultured may be of any type and may be cultivated in part or as a whole. They may be, for example, fragments of roots, leaves or stems or even flower buds or opened flowers.

The plants or organs may be of any origin, i.e.,
- either obtained by harvesting of cultivated or collected plants, in which case the process enables utilization of traditional vegetable production to be improved by extension of the biosynthesis and production phase of the desired substances,
- or formed from cell cultures, in which case the process provides for complete independence from traditional culture.

The plants or vegetable organs may be decontaminated before their implantation in the culture medium to eliminate troublesome microorganisms. The plants or organs may be decontaminated by immersion for a few minutes in a decontaminating solution, such as Javel water, mercury dichloride, calcium or sodium hypochlorite or any other typical decontaminant or by any other chemical or physical means (X rays, $\gamma$ rays, etc.).

The culture medium used should provide the vegetable organ with the nutrients necessary for its survival in the production phase. This nutrient medium may be in semisolid form (aqueous gelose) or in the form of an optionally stirred liquid to simplify culture of the vegetable organs. In the latter case, culturing may merely amount to immersion of the decontaminated organs in the nutrient medium followed by covering with a film of oil to avoid any changes in the surface.

The culture medium may be renewed so that the organ is always supplied with the elements necessary for its survival and to remove any diffused compounds (antagonistic and/or desired) therefrom. Renewal of the culture medium may be continuous or semi-continuous.

Similarly, the culture medium may be modified by addition of growth regulators and/or by addition of elements capable of promoting production of the desired metabolites (addition of precursors).

The culture medium is preferably a medium of the type typically used in the "in vitro" culture of tissues, such as a Gamborg medium, Heller medium or even Murashige and Skoog medium, of which the compositions are shown in Table I below. The preferred culture medium according to the invention is Gamborg medium.

The oil used to cover the vegetable organ may perform two functions, namely:
- it acts first and foremost as a preservative, ensuring the maintenance of hypoxia and
- it may act as a trapping/extracting agent for the desired lipophilic substances.

The choice of the oil is dependent on certain criteria, such as:
- its ability to cause hypoxia, i.e., to transfer no external oxygen or very little external oxygen to the vegetable organ and its culture medium,
- its dissolving power on the desired substances,
- its absence of toxicity with respect to the vegetable organs.

Since it is preferred to renew the oil periodically, because it can become saturated by extraction of the desired substances, a liquid hypoxia medium is easier to handle than a solid medium, although a solid medium may be used. The oil may be renewed continuously or semi-continuously.

Suitable oils include oils of mineral, organic or vegetable origin, synthetic oils and any other oil capable of acting as a preservative. The preferred oil according to the invention is a paraffin oil.

The oil may be degassed and sterilized before use. Degassing may be carried out by placing the oil under vacuum, the gases present therein escaping and optionally being replaced by nitrogen.

To avoid the degradation of chlorophyll, which could adversely affect survival of the vegetable organ, low lighting of the order of 0–400 lux may be used in the application of the process according to the invention. The culture temperature may be in the range from 18° C. to 35° C. and is preferably of the order of 25° C.

The process according to the invention for the production of substances of a vegetable origin may be carried out discontinuously, semi-continuously or continuously.

EXAMPLES

The invention is illustrated in more detail in the following Examples. Examples A, B and C relate more particularly to sustenance and to the criteria used for its evaluation. The Examples are preceded by the following Table which shows the composition of the culture medium used.

TABLE I

| Composition of the media used (pH = 5.8) | | | |
|---|---|---|---|
| | Murashige and Skoog medium mg/l | Gamborg medium mg/l | Heller medium mg/l |
| Sucrose | 20000 | 20000 | 20000 |
| Agar (media treated with gelose) | 8000 | 8000 | 8000 |
| Macro elements | | | |
| $NH_4NO_3$ | 1650 | — | — |
| $(NH_4)_2SO_4$ | — | 134 | — |
| $CaCl_2 \cdot H_2O$ | 440 | 150 | 75 |
| $MgSO_4 \cdot 7H_2O$ | 370 | 250 | 250 |
| KCl | — | — | 750 |
| $KNO_3$ | 1900 | 2500 | — |
| $KH_2PO_4$ | 170 | — | — |
| $NaNO_3$ | — | — | 600 |
| $NaH_2PO_4 \cdot H_2O$ | — | — | 125 |

TABLE I-continued

| Composition of the media used (pH = 5.8) | | | |
|---|---|---|---|
| | Murashige and Skoog medium mg/l | Gamborg medium mg/l | Heller medium mg/l |
| Micro elements | | | |
| $AlCl_3 \cdot 6H_2O$ | — | — | 0.05 |
| $CoCl_2 \cdot 6H_2O$ | 0.025 | 0.025 | — |
| $CuSO_4 \cdot 5H_2O$ | 0.025 | 0.025 | — |
| $FeCl_3 \cdot 6H_2O$ | — | — | 1.0 |
| $FeSO_4 \cdot 7H_2O$ | 27.8 | 27.8 | 27.8 |
| $Na_2$-EDTA | 37.3 | 37.3 | 37.3 |
| $MnSO_4 \cdot 4H_2O$ | 22.3 | 10.0 | 0.1 |
| $NiCl_2 \cdot 6H_2O$ | — | — | 0.03 |
| KI | 0.83 | 0.75 | 0.01 |
| $Na_2MoO_4 \cdot 2H_2O$ | 0.25 | 0.25 | — |
| $ZnSO_4 \cdot 7H_2O$ | 8.6 | 2.0 | 1.0 |
| $H_3BO_3$ | 6.2 | 3.0 | 1.0 |
| Vitamins | | | |
| Calcium pantothenate | — | — | 1 |
| Meso-inositol | 100 | 100 | 100 |
| Nicotinic acid | 10.5 | 1 | 1 |
| Pyridoxine (vit. $B_6$) | 0.5 | 1 | 1 |
| Thiamin (vit. $B_1$) | 0.1 | 10 | 1 |
| Biotin | — | — | 0.1 |

EXAMPLE A

Fragments of fennel stems are decontaminated by immersion for a few minutes in a solution of calcium hypochlorite and thorough rinsing in sterile distilled water. These fragments are then implanted in a Gamborg medium solidifed by addition of agar agar. They are then placed under hypoxia by addition of sterilized paraffin oil and left standing at 25° C. in low light (200 lux). The evolution of the pigmentation of the fennel stems placed under hypoxia by comparison with similar stems placed in the same nutrient medium, but without the added oil, is observed over a period of 18 weeks.

After 6 weeks, all the stems under hypoxia are still green without any sign of chlorosis whereas the comparison stems all show incipient chlorosis. 30% of the comparison stems are affected by oxidation or total chlorosis after 8 weeks whereas only 10% of the stems under hypoxia show incipient chlorosis after the same period and only 20% after 12 weeks. At 16 weeks, 90% of the comparison stems are completely oxidized against 40% for the stems under hypoxia, the rest still remaining green. After 18 weeks, 100% of the comparison stems are completely oxidized whereas only 50% of the stems under hypoxia are completely oxidized, the remaining 50% showing only incipient chlorosis. Finally, after 6 weeks, none of the comparison stems is completely green whereas 50% of the stems under hypoxia are still completely green after 16 weeks.

EXAMPLE B

Flower buds of tuberose are collected at three different stages of development, namely:
- stage I: corolla 1–1.5 cm long—green petals
- stage II: corolla 2 cm long—beginning of whitening of the petals
- stage III: corolla 3 cm long—white petals They are decontaminated and implanted in a Gamborg medium treated with gelose. The buds are then placed under hypoxia by addition of paraffin oil. No oil is added to the comparison buds. The whole is left under low light (200 lux) at 25° C.

The evolution of the oxidation of these flower buds as a function of time is recorded arbitrarily on a scale of 0 to 7 in which 0 = absence of oxidation patches
1 = beginning of oxidation at the ends of the petals on at most 10% of the petals
2 = beginning of oxidation at the ends of the petals on more than 10% of the petals
3 = oxidation of half the surface area of the petals on at most 10% of the petals
4 = oxidation of half the surface area of the petals on more than 10% of the petals
5 = oxidation of half the surface area of the petals on more than 50% of the petals
6 = significant oxidation of the flower (80%)
7 = complete oxidation of the flower.

It should be noted that the addition of antioxidants to the paraffin oil does not bring about any significant reduction in oxidation.

The use of degassed oil does not produce any significant difference in relation to non-degassed oil. By contrast, there is a clear difference between the buds placed under hypoxia and the comparison buds.

The following Tables show the evolution of the degree of oxidation as a function of time: For the buds at stage I:

| Time (days) | 2 | 5 | 7 | 10 | 13 | 17 | 18 | 24 | 28 |
|---|---|---|---|---|---|---|---|---|---|
| Comparison | 0 | 0 | 1 | 1 | 5 | 5 | 6 | 7 | 7 |
| Oil | 0 | 0 | 0 | 1 | 1 | 1 | 2 | 2 | 3 |
| Degassed oil | 0 | 0 | 0 | 1 | 1 | 1 | 2 | 2 | 3 |

It can be seen that the comparison buds are completely oxidized after 24 days whereas the buds under hypoxia survive for more than 4 weeks. For the buds at stage II:

| Time (days) | 2 | 5 | 7 | 10 | 13 | 17 | 18 | 24 | 28 |
|---|---|---|---|---|---|---|---|---|---|
| Comparison | 0 | 0 | 2 | 2 | 5 | 7 | 7 | 7 | 7 |
| Oil | 0 | 0 | 0 | 1 | 1 | 1 | 1 | 2 | 2 |
| Degassed oil | 0 | 0 | 0 | 1 | 1 | 1 | 1 | 2 | 2 |

The comparison buds are oxidized after 17 days whereas the buds under hypoxia are only slightly oxidized after 4 weeks. For the buds at stage III:

| Time (days) | 2 | 5 | 7 | 10 | 13 | 17 | 18 | 24 | 28 |
|---|---|---|---|---|---|---|---|---|---|
| Comparison | 2 | 5 | 7 | 7 | 7 | 7 | 7 | 7 | 7 |
| Oil | 0 | 0 | 1 | 1 | 2 | 3 | 3 | 4 | 4 |
| Degassed oil | 0 | 1 | 1 | 2 | 3 | 4 | 4 | 5 | 5 |

The comparison buds are oxidized after 7 whereas the buds under oil can be kept for up to 28 days before being completely oxidized.

EXAMPLE C

Various vegetable organs were decontaminated, implanted in a Gamborg medium treated with gelose, then placed under hypoxia beneath a layer of paraffin oil and left at 25° C. in low light (200 lux). The vegetables include aromatic plants (I), perfume plants (II) and plants which do not produce an aroma, but do produce non-volatile substances of pharamcological or cosmetic value (III).

The results of these tests are shown in the following Table:

| | Species | Organs | Possible survival under hypoxia |
|---|---|---|---|
| I | Ocimum basilicum | leaves | 10–12 weeks |
| | Verbena triphylia | leaves | 3–4 weeks |
| II | Pelargonium capitatum | leaves | 8–10 weeks |
| | Pogostemon patchouli | leaves | 8–10 weeks |
| III | Ferula galbanum | roots | 10–12 weeks appearance of calluses |
| | Gingko biloba | leaves | 14–16 weeks |

Irrespective of the type of plant or organ implanted, survival under hypoxia is possible for at least one month and may be maintained for as long as four months.

EXAMPLE 1

Mint leaves which have been decontaminated and then implanted in a Gamborg medium are placed under hypoxia beneath a layer of paraffin oil at 25° C. The production of aromatic compounds during the survival phase is followed over a period of 5 weeks. The mint leaves are divided into three groups and subjected to different experimental conditions:

group A: strong light (2000 lux)
group B: low light (200 lux)
group C: strong light (2000 lux) and addition of terpene precursor.

The presence in the oil of a compound characteristic of the essential oil, namely carvone, is particularly followed. The oil is regularly renewed over a period of 35 days in the three groups and a quantitative analysis is performed by densitometry through thin-layer chromatography to determine the quantity of carvone present in the oil collected. The results are confirmed by analysis by gas-phase chromatography. The following Table shows the quantity of carvone which has collected in the oil for the three groups over a period of 5 weeks. The quantity of carvone is expressed in micrograms per gram fresh implanted leaf material.

| Time (days) | 1 | 2 | 3 | 4 | 7 | 14 | 21 | 28 | 35 |
|---|---|---|---|---|---|---|---|---|---|
| Group A | 20 | 60 | 10 | 240 | 10 | 170 | 120 | 240 | 110 |
| Group B | 110 | 60 | 10 | 20 | 20 | 20 | 20 | 140 | 110 |
| Group C | 620 | 60 | 80 | 10 | 170 | 170 | 260 | 340 | 170 |

A peak is observed in the production of carvone at the beginning of kinetics, followed by a fall in production and then by a resumption with a new accumulation peak at 28 days.

The following Table shows the increase in the accumulation of carvone over the 35 day period (in $\mu g/g$ fresh material).

| | I | II | III | IV |
|---|---|---|---|---|
| Group A | 690 | 980 | 635 | 925 |
| Group B | 690 | 510 | 600 | 520 |
| Group C | 690 | 1880 | 820 | 2010 |

I: initial carvone content in the implanted leaf
II: carvone accumulated in the oil over 35 days
III: final carvone content of the residual tissues
IV: increase in carvone over 35 days (II+III−I).

These figures clearly illustrate the resumption in the synthesis of carvone over a period of time rather than a simple solid/liquid extraction phenomenon; the total produced may reach three times the quantity present in the initial implant.

EXAMPLE 2

Fennel stems according to Example A are cultivated in vitro under paraffin oil in a Gamborg medium treated with gelose. The synthesis of p-allyl anisole, a compound characteristic of the essential oil, during the survival phase, is followed over a period of 2 months.

The fennel stems are divided into three groups which are subjected to different experimental conditions:

Group A: basic Gamborg medium
sucrose: 20 g $l^{-1}$
lighting 200 lux

Group B: basic Gamborg medium + growth regulator
sucrose: 20 g $l^{-1}$
lighting: 200 lux Group C: 1/10 basic Gamborg medium
sucrose: 10 g $l^{-1}$
lighting: 200 lux The paraffin oil is regularly renewed after 1, 3, 5 and 7 weeks and then analyzed quantitatively and qualitatively by gas-phase chromatography. The presence of p-allyl anisole in the oil and the appearance of numerous other aromatic compounds are noted.

The following Table shows the quantity of p-allyl anisole which has accumulated in the oil (in μg/g of fresh implanted leaf material) as a function of time:

|         | Time (days) |    |    |        |     |     |     |     |
|---------|-------------|----|----|--------|-----|-----|-----|-----|
|         | 7           | 21 | 35 | 49     | I   | II  | III | IV  |
| Group A | 222         | 42 | 122| traces | 333 | 386 | 35  | 88  |
| Group B | 400         | 48 | 42 | traces | 333 | 490 | 30  | 187 |
| Group C | 291         | 94 | 52 | 136    | 333 | 573 | 106 | 346 |

I: initial p-allyl anisole content of the implanted stem
II: p-allyl anisole accumulated in the oil
III: final p-allyl anisole content of the residual tissues
IV: increase in p-allyl anisole over 7 weeks (II+III−I)

The total production can reach twice that of the implant (group C).

We claim:

1. A process for producing vegetable-derived substances, including essential oils, from vegetable organs comprising implanting a vegetable organ of differentiated cells in a culture medium, covering the implanted vegetable organ with oil for sustaining the vegetable organ in the culture medium under hypoxia while culturing the oil-covered vegetable organ and subsequently extracting substances of vegetable origin from the oil, wherein the vegetable organ is at least a part of a vegetable organ selected from the group of vegetable organs consisting of roots, stems, leaves, flowers and flower buds.

2. A process according to claim 1 wherein the culture medium contains growth regulators.

3. A process according to claim 1 wherein the culture medium contains precursors for promoting production of metabolites by the cultured vegetable organ.

4. A process according to claim 1 further comprising culturing the vegetable organ under a light up to 400 lux.

5. A process according to claim 1 wherein the vegetable organ is cultured at a temperature of from 18° C. to 35° C.

6. A process according to claim 1 further comprising decontaminating the vegetable organ prior to implanting it in the culture medium.

7. A process according to claim 1 wherein the oil is a degassed and sterilized oil.

8. A process according to claim 1 wherein the oil is an oil selected from the group of oils consisting of oil of mineral origin, organic origin, vegetable origin and synthetic origin.

9. A process according to claim 1 wherein the oil is paraffin oil.

10. A process according to claim 1 further comprising renewing the culture medium during culturing.

11. A process according to claim 1 further comprising renewing the oil during culturing of the vegetable organ.

12. A process according to claim 1 wherein the vegetable organ is a member selected from the group consisting of mint leaves and fennel stems.

* * * * *